(12) United States Patent
DeGeeter

(10) Patent No.: US 9,937,147 B2
(45) Date of Patent: *Apr. 10, 2018

(54) EDIBLE BASE PRODUCT COMPOSITION

(71) Applicant: NBDD, Inc., San Francisco, CA (US)

(72) Inventor: Doug DeGeeter, San Francisco, CA (US)

(73) Assignee: NBDD, Inc., San Francisco, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/336,710

(22) Filed: Oct. 27, 2016

(65) Prior Publication Data

US 2017/0119728 A1    May 4, 2017

Related U.S. Application Data

(63) Continuation-in-part of application No. 14/927,356, filed on Oct. 29, 2015, now Pat. No. 9,526,792.

(51) Int. Cl.

| | |
|---|---|
| *A61K 36/00* | (2006.01) |
| *A61K 31/352* | (2006.01) |
| *A23L 33/105* | (2016.01) |
| *A23L 33/115* | (2016.01) |
| *A23P 10/28* | (2016.01) |
| *A23L 33/125* | (2016.01) |
| *A61K 9/20* | (2006.01) |
| *A61K 36/185* | (2006.01) |
| *A61K 47/24* | (2006.01) |
| *A61K 47/36* | (2006.01) |
| *A61K 47/46* | (2006.01) |

(52) U.S. Cl.
CPC .......... *A61K 31/352* (2013.01); *A23L 33/105* (2016.08); *A23L 33/115* (2016.08); *A23L 33/125* (2016.08); *A23P 10/28* (2016.08); *A61K 9/205* (2013.01); *A61K 9/2013* (2013.01); *A61K 9/2068* (2013.01); *A61K 36/185* (2013.01); *A61K 47/24* (2013.01); *A61K 47/36* (2013.01); *A61K 47/46* (2013.01); *A23V 2002/00* (2013.01)

(58) Field of Classification Search
CPC ...................................................... A61K 36/00
USPC ......................................................... 424/725
See application file for complete search history.

(56) References Cited

U.S. PATENT DOCUMENTS

| | | | |
|---|---|---|---|
| 1,965,490 | A | 7/1934 | Conway et al. |
| 4,882,164 | A | 11/1989 | Ferro et al. |
| 5,302,409 | A | 4/1994 | Franklin |
| 5,364,455 | A | 11/1994 | Komarneni |
| 8,486,475 | B2 | 11/2013 | Villagran et al. |
| 9,629,886 | B2 | 4/2017 | Franklin |
| 2014/0271940 | A1 | 9/2014 | Wurzer |

FOREIGN PATENT DOCUMENTS

| | | | |
|---|---|---|---|
| CN | 103355726 A | * | 8/2013 |
| WO | 9611581 A1 | | 4/1996 |
| WO | 2009061222 A2 | | 11/2008 |

* cited by examiner

*Primary Examiner* — Michael V Meller
(74) *Attorney, Agent, or Firm* — Temmerman Law Office; Mathew J. Temmerman

(57) ABSTRACT

A composition of an edible base product, the composition comprising a cannabis concentrate containing at least one cannabinoid, a starch concentrate containing tapioca maltodextrin, a rice concentrate, and a lipid concentrate containing lecithin. The method of producing the composition comprises sheering the ingredients at a proper temperature in a dry environment. Preferably, the rice concentrate acts as a natural desiccate and silicate and also an anti-caking agent. The lecithin is added to the powdered cannabis concentrate to enhance the absorption of THC into the blood stream of the individuals.

19 Claims, No Drawings

EDIBLE BASE PRODUCT COMPOSITION

RELATED INVENTIONS

This application is a continuation-in-part application of nonprovisional utility patent application Ser. No. 14/927,356, filed Oct. 29, 2016, which is currently pending and for which a notice of allowance has issued. The disclosures of that application is incorporated herein by reference as if set out in full.

BACKGROUND OF THE DISCLOSURE

Technical Field of the Disclosure

The present embodiment relates in general to edible/sublingual compositions. More specifically, the present disclosure relates to a composition incorporating cannabis concentrates that are employed as an edible base product for use in a wide variety of medicinal and culinary applications.

Description of the Related Art

Cannabis concentrates are the extracted resins obtained from green leafy marijuana or cannabis containing cannabinoids including tetrahydrocannabinol (THC), cannabidiol (CBD), CBN, CBS, THCV, CBG and other major and minor phytocannabinoids. Resinous cannabis extracts include, but are not limited to butane hash oil, wax, cannabutter, C02 extracted cannabinoids and other cannabis infusions, and extractions which are extremely potent cannabis concentrates. These resinous cannabis concentrates are popularly consumed by "dabbing" and other vaporization methods. Concentrated cannabis resins are difficult to work with in a culinary application due to their high viscosity levels. At room temperature such resins have the consistency of tree sap or tar and in use can be burdensomely sticky. When resinous cannabis concentrates are heated they become a very thick, dense, sticky substance. By converting concentrated cannabis resins, extracts and fat based infusions into powdered form they become not only readily available for ingestion, but can be easily stored, packaged and made readily available for use with little hassle or inconvenience. The cannabis extractions can now be accurately measured and portioned in the amount needed from the master batch. The powdered form is adaptable to provide better consistency in the distribution of these cannabis concentrates when applied to edible and sublingual preparations. It also aids in the accurate application of cannabinoids to a preparation to obtain a specified volume of cannabinoids per portioned batch of the preparation.

Current cannabis compositions developed for edible uses are not ready to use directly from storage without tempering to the proper temperature. Some cannabis compositions currently available cannot be used for sub-lingual ingestion and do not enhance the absorption of cannabinoids into the blood stream of individuals faster than existing ingested edibles. Some of the traditional cannabis compositions contain flour or gluten which consume more time during the cooking process. Furthermore, certain conventional cannabis compositions can cause the production of botulism and other microbial contaminates and food born illnesses if improperly stored or in some cases during normal storage when oil infusions are involved.

Given the forgoing, there is a need for an easily produced powdered cannabis product that can be employed as an edible base product for use in a wide variety of medicinal and culinary applications. For purposes of this process, tapioca maltodextrin is used as a medium to produce powdered cannabis concentrates to make them easily ingestible. Tapioca maltodextrin is a light weight bulking agent derived from tapioca starch and when it is mixed with fat, it has the ability to absorb it and transform the fat into a powder like substance. Tapioca maltodextrin is traditionally used to bulk up fats or to thicken fats in commercial food production. When tapioca maltodextrin used in high enough amounts it drastically alters the texture of fats.

Cannabis compositions can be mixed with flavoring products or oils for culinary applications. However, this process requires cooking which is a time consuming process; and often when the compositions are mixed with other flavoring products or oils their shelf-life is drastically reduced.

Therefore, there is a need for a powdered culinary oriented cannabis composition with a wide variety of culinary applications that is employed as an edible or sublingual base product useable for a wide variety of medicinal and culinary applications. Such a composition would include tapioca maltodextrin that is mixed with the concentrated resinous secretions or fat based extractions of the cannabis plant in a controlled manner to create a potent powdered form of cannabis concentrate without altering the properties of the cannabinoids including THC, CBD, CBN, CBC, THCV, CBG and other cannabinoids present. Such a needed method would provide an edible powdered cannabis product with a stable shelf-life, ready-to-use directly from storage or the freezer with no need for tempering to room temperature before measuring. This composition would be mixed with other food products using standard food grade mixing equipment, without the need for cooking. Such a method would provide an edible powdered cannabis product which because it replaces infused oils is free from potential microbiological problems like botulism, *e. coli*, and *salmonella* while being stored or manufactured. Because this method would also provide an edible powdered cannabis which enhances the absorption of cannabinoids into the blood stream faster than existing ingested edibles, this composition is suitable for use as a sub-lingual ingestion method.

To minimize the limitations found in the prior art, and to minimize other limitations that will be apparent upon the reading of the specification, the preferred embodiment of the present invention provides a composition incorporating cannabis concentrates that are employed as an edible base product useable for a wide variety of medicinal and culinary applications. The composition comprises a cannabis concentrate containing at least one cannabinoid compound, a starch concentrate containing tapioca maltodextrin, a rice concentrate, and a lipid concentrate containing lecithin. The composition was prepared in a high speed sheering device by sheering the ingredients at proper temperature in a dry environment. The at least one cannabinoid compound is selected from the group consisting of cannabinol, tetrahydrocannabinol (THC), cannabidiol (CBD), Tetrahydrocannabinol acid, cannabidiol acid, tetrahydrocannabivarin, cannabidivarin, dronabinol, amandamide, nabilone, and combinations thereof. The tapioca maltodextrin is a medium used to produce powdered cannabis concentrate for easy ingestion. The rice concentrate acts as a natural silicate, desiccate and an anti-caking agent. Preferably, the lecithin is added to the powdered cannabis concentrate to enhance the absorption of cannabinoids into the blood stream of the individuals while consumption.

The present invention also contemplates a method for producing an edible base product that comprises of shearing a 1:1:1 ratio of a cannabis concentrate by weight containing at least one cannabinoid compound, adding a starch concentrate by weight containing tapioca maltodextrin, adding lipid concentrate containing lecithin and 2% of a rice concentrate by weight, adding and sheering the total ingredients in a high speed sheering device to obtain an edible composition.

Unless noted otherwise, all percentages recited in the specification and accompanying claims refer to a weight percentage.

A first objective of the present invention is to provide a composition containing powdered cannabis concentrates that are employed as an edible base product useable for a wide variety of medicinal and culinary applications.

A second objective of the present invention is to provide an edible powdered cannabis concentrates with a stable shelf-life, ready-to-use directly from the freezer or other storage with no need for tempering to room temperature.

A third objective of the present invention is to provide an edible powdered cannabis concentrates that enhances the absorption of cannabinoids into the blood stream of individuals faster than existing ingested edibles.

A fourth objective of the present invention is to provide an edible powdered cannabis concentrates which is free from potential microbiological problems such as botulism while being stored.

Another objective of the present invention is to provide an edible powdered cannabis concentrates that is suitable for use as a sub-lingual ingestion method.

Another objective of the present invention is to provide a composition that is used as an easy and accurate means for precisely controlling dosage amounts of cannabinoid concentrates and extracts for individuals to treat medical conditions and symptoms.

These and other advantages and features of the present invention are described with specificity so as to make the present invention understandable to one of ordinary skill in the art.

Another objective of the present invention is to provide a non-natural application of the invention that would include the ability to produce both tablets and capsule forms. Because the composition has the ability for precise dosage control and the tapioca maltodextrin medium has the ability to be applied to a multitude of preparations non-natural application are a logical extension of the applied uses of the invention.

DETAILED DESCRIPTION OF THE DISCLOSURE

In the following discussion that addresses a number of embodiments and applications of the present invention in which the invention may be practiced. It is to be understood that other embodiments may be utilized and changes may be made without departing from the scope of the present invention.

Various inventive features are described below that can each be used independently of one another or in combination with other features. However, any single inventive feature may not address any of the problems discussed above or only address one of the problems discussed above. Further, one or more of the problems discussed above may not be fully addressed by any of the features described below.

The present invention comprises edible compositions and methodology for forming edible and sublingual compositions. The base composition encompassed by the present invention comprises a cannabis concentrate and a starch concentrate containing tapioca maltodextrin. In addition, the invention relates to the process for providing such "ready-for-use" compositions and the improved food products prepared from the co-processed compositions. The composition further comprises a rice concentrate and a lipid concentrate containing lecithin. Preferably, the rice concentrate is Nu-Flow® rice bran concentrate from Ribus, Inc.

The cannabis concentrate comprises at least one cannabinoid compound. The at least one cannabinoid compound is selected from the group consisting of cannabinol, tetrahydrocannabinol (THC), cannabidiol (CBD), Tetrahydrocannabinol acid, cannabidiol acid, tetrahydrocannabivarin, cannabidivarin, dronabinol, amandamide, nabilone, and combinations thereof. The cannabis concentrate is present in the composition in an amount of about 33% by weight. The cannabis concentrate is extracted from resinous secretions of cannabis plant.

In one embodiment, the cannabis concentrate of the present invention can be used to create various cannabis products. Cannabis products include: canna-butter, solvent reduced oils such as hash oils, co2 extracts and other cannabinoid infused oils as well as any other fat soluble resinous cannabis secretions.

In one embodiment, the starch concentrates can be derived from a variety of sources including, but not limited to, cereal, tuber, legumes, fruits and vegetable starches. The starch may be modified and/or unmodified and those of skill in the art will understand how to select from one or more of the starches that may be used in the present invention. For example, the starch concentrates is not limited to tapioca maltodextrin and may include corn, waxy maize, sweet potato, potato, canna, arrowroot, sorghum, waxy sorghum, waxy rice, sago, rice, etc., as well as mixtures thereof. The starch concentrate is present in the composition in an amount of about 33% by weight.

In one embodiment of the present invention, the starch concentrate contains tapioca maltodextrin. The maltodextrin is preferably a low DE type, typically less than 20 and is preferably a 10 DE maltodextrin. The tapioca has a unique property of absorbing its own weight in fat. It is believed that the combination of the cannabis concentrate and tapioca maltodextrin produce a powdered form of the cannabis concentrate to make the cannabis concentrate easily ingestible. The combination of the cannabis concentrate and tapioca maltodextrin allows an individual to make the composition into portions of desirable intake amounts. The powdered form of the cannabis concentrate and tapioca maltodextrin can be stored and readily available for use with little hassle or inconvenience in measuring out precisely to the hundredth of the gram the amount needed from the master batch.

In one embodiment, the cannabis concentrate is extracted from resinous secretions of cannabis plant. A decarboxylation step may be carried out prior to or after extraction using a solvent. The cannabinoids exist in two forms, as acids and in neutral (decarboxylated) forms. The biologically active forms for human consumption are the neutral forms. The decarboxylation of cannabinoid acid is usually achieved by thorough drying of the plant material followed by heating it, often by either combustion, vaporization, or heating or baking in an oven. Decarboxylation of cannabinoid acids is a function of time and temperature, thus at higher temperatures a shorter period of time will be taken for complete decarboxylation of a given amount of cannabinoid acid. The tapioca maltodextrin is added to concentrated resinous secretions of the cannabis plant in a controlled manner to create a very potent powdered form of the cannabis concentrate without altering the properties of THC and the other cannabinoids. The rice concentrate is applied to increase the flow of the composition and reduce caking due to atmosphere moisture. Preferably, lecithin is added to the cannabis concentrates during the to enhance the absorption of cannabinoids, both decarboxylated and not, into the blood stream.

The rice concentrate (preferably NU-Flow® by RIBUS, Inc, of St. Louis, Mo.) is present in the composition in an amount of about 2% by weight (total weight by volume, not baker's percentage), and acts as a natural desiccate and silicate to aid as an anti-caking agent. The rice concentrate may be added to the powdered cannabis to aid in the commercial production, storage and packaging of the powdered cannabis. The rice concentrate is a food product that replaces the anti-caking agent SiO2 tri-calcium phosphate, and meets organic labeling guidelines.

The lecithin is adaptable to bind with the cannabinoid molecules and enhance the absorption rate of cannabinoids during consumption. The lecithin is present in the composition in an amount of about 33% by weight. The lipid concentrate including, but not limited to lecithin, sunflower lecithin, soy lecithin, egg lecithin, peanut lecithin, sesame lecithin, canola lecithin, and combinations thereof.

In one embodiment, the invention provides a method for producing an edible base product which comprises
a) adding 100 gr of a cannabis concentrate by weight containing at least one cannabinoid compound;
b) adding 100 gr of a starch concentrate by weight containing tapioca maltodextrin;
c) adding 2% of a rice concentrate by weight;
d) adding 100 gr of a lipid concentrate containing lecithin; and
e) sheering and blending the total ingredients of steps (a) to (d) in a high speed sheering device to obtain an edible composition.

EXAMPLES

The following examples illustrate, but do not limit, the present invention. Unless otherwise indicated, all parts and percentages are by weight.

Example 1

The following example provides suitable ranges of ingredients for one embodiment of the present invention. In this embodiment, the concentrated form of the product is presented in the following Table 1.

The concentrated form of the composition was prepared from the following ingredients.

TABLE 1

| Ingredients | Amount (wt/wt) |
| --- | --- |
| Cannabis concentrates | 100 gr |
| Tapioca maltodextrin | 100 gr |
| Nu-Flow ® | 6 gr |
| Lecithin | 100 gr |
| Total | 306 gr |

All percentages are by weight of the composition.

The composition was prepared in a high speed sheering device by sheering the ingredients using the method described earlier in this specification at proper temperature in a dry environment.

Example 2

The following example provides suitable ranges of ingredients for one embodiment of the present invention. In this embodiment, the consumption form (intake by the individuals) of the product is presented in the following Table 2.

The consumption form of the composition was prepared from the following ingredients.

TABLE 2

| Ingredients | Amount (wt/wt) |
| --- | --- |
| Cannabis concentrates | 1 gr |
| Tapioca maltodextrin | 100 gr |
| Nu-Flow ® | 2.6 gr |
| Lecithin | 20 gr |
| Total | 123.6 gr |

All percentages are by weight of the composition.

The composition was prepared in a high speed sheering device by sheering the ingredients using the method described earlier in this specification at proper temperature in a dry environment.

Example 3

The following example provides suitable ranges of ingredients for one embodiment of the present invention. In this embodiment, the additive form (used as additive for other food products) of the product is presented in the following Table 3.

The additive form of the composition was prepared from the following ingredients.

TABLE 3

| Ingredients | Amount (wt/wt) |
| --- | --- |
| Cannabis concentrates | 50 gr |
| Tapioca maltodextrin | 100 gr |
| Nu-Flow ® | 1 gr |
| Lecithin | 50 gr |
| Total | 204 gr |

All percentages are by weight of the composition.

The composition was prepared in a high speed sheering device by sheering the ingredients using the method described earlier in this specification at proper temperature in a dry environment.

The above listed ingredients comprise less fat than prior art compositions, meaning that more fatty food products can be mixed with the composition for flavoring. For instance, natural organic oils for chocolate manufacturing are good fats to add because they are essential oils having a stable shelf-life. The other food products are mixed with the composition by sheering at high speed in a sheering device without the need for cooking. For example, dry caramel, freeze dried fruits and vegetables, and other suitable ingredients which are in freeze dried or moisture free form may be blended with the composition. The property of the composition may vary with the property of additional food based additives added to the composition.

This composition is used as an easy and accurate means for controlling dosage amounts for cannabinoid concentrates and extracts. The composition is suitable for use as a sublingual ingestion method. This composition enhances the absorption of cannabinoids into the blood stream of the individuals 2 to 3 times faster than existing ingested edibles. The edible powdered cannabis is free from potential problems like botulism and other food born illnesses while being stored. The composition may be used in a wide variety of commercial food production applications, i.e. salad dressings, ice creams and yogurts, cake mixes, flavorings for chips and nuts, seasoning, instant sauces, etc. The composition has a stable shelf-life, ready-to-use directly from the freezer or other storage without thawing or tempering before portioning, i.e., it is easy to portion and scale directly from the freezer. The frozen powdered cannabis concentrates minimize the loss of the product while handling while pure form cannabis concentrates stick to virtually everything with the exception of silicon, additionally it is tricky to accurately transfer the concentrate (non-powered) while maintaining accurate measurement of the material due to its tacky texture. Individuals having health issues and dietary restriction for using traditional forms of cannabis edibles can safely use the present composition in a desirable amount.

The present invention in tablet form can be made in both flavored and unflavored forms and would lend itself to packaging in current child safe packaging systems, and could be created in a variety of dosages suited for individual needs. In chewable form, they tablets may be ingested as both an edible or sublingual cannabinoid ingestion method. In capsule form the present invention may be unflavored or flavored. The capsules may be created in specific cannabinoid milligram amounts and could be packaged in existing child safe packaging used for pharmaceuticals and medicines. The capsule form may also be ingested directly as a capsule or because the contents are food based emptied and used in culinary preparations with confidence in dosage amounts. Both the capsule and tablet form lend themselves to automated production and packaging methods for upwards scalability.

It should be apparent that various modifications and changes can be made both in the processing and in the relative amounts of the preferred ingredients to prepare food products without departing from the scope of the invention set forth in the claims. All such modifications or changes coming within the terms of the claims are intended to be included in the claims. Although the invention has been described with reference to certain specific embodiments, various modifications thereof will be apparent to those skilled in the art without departing from the spirit and scope of the invention. All such modifications as would be apparent to one skilled in the art are intended to be included within the scope of the following claims.

What is claimed is:

1. A tablet or capsule consisting essentially of:
   a cannabis concentrate containing at least one cannabinoid compound;
   tapioca maltodextrin as a medium to allow the cannabis concentrate to be easily ingestible; and
   a rice concentrate;
   wherein the cannabis concentrate is present in the composition in an amount of about 33% by weight.

2. The tablet or capsule of claim 1, wherein the at least one cannabinoid compound is selected from the group consisting of cannabinol, tetrahydrocannabinol, cannabidiol, tetrahydrocannabinol acid, cannabidiol acid, tetrahydrocannabivarin, cannabidivarin, dronabinol, amandamide, nabilone, and combinations thereof.

3. The tablet or capsule of claim 1, wherein the cannabis concentrate is extracted from resinous secretions of a cannabis plant.

4. The tablet or capsule of claim 1, wherein the tapioca maltodextrin is present in the tablet or capsule in an amount of about 33% by weight.

5. The tablet or capsule of claim 1, further consisting essentially of a lipid concentrate.

6. The tablet or capsule of claim 5, wherein the lipid concentrate is adaptable to enhance the absorption rate of cannabinoids during consumption.

7. The tablet or capsule of claim 1, wherein the lipid concentrate is present in the tablet or capsule in an amount of about 33% by weight.

8. The tablet or capsule of claim 5, wherein the lipid concentrate is a lecithin.

9. The tablet or capsule of claim 1, wherein the rice concentrate is present in the tablet or capsule in an amount of about 2% by weight.

10. The tablet or capsule of claim 1, wherein the rice concentrate acts as a natural silicate and desiccate and an anti-caking agent.

11. A tablet or capsule consisting essentially of:
    a cannabis concentrate containing at least one cannabinoid compound extracted from resinous secretions of cannabis plant;
    tapioca maltodextrin;
    a rice concentrate; and
    lecithin.

12. The tablet or capsule of claim 11, wherein the at least one cannabinoid compound is selected from the group consisting of cannabinol, tetrahydrocannabinol, cannabidiol, tetrahydrocannabinol acid, cannabidiol acid, tetrahydrocannabivarin, cannabidivarin, dronabinol, amandamide, nabilone, and combinations thereof.

13. The tablet or capsule of claim 11, wherein the cannabis concentrate is present in the tablet or capsule in an amount of about 33% by weight.

14. The tablet or capsule of claim 11, wherein the tapioca maltodextrin is used as a medium to produce powdered cannabis concentrates to make the powdered cannabis concentrate easily ingestible.

15. The tablet or capsule of claim 11, wherein the tapioca maltodextrin is present in the tablet or capsule in an amount of about 33% by weight.

16. The tablet or capsule of claim 11, wherein the lecithin is adaptable to bind with THC molecules and enhance an absorption rate of THC during consumption.

17. The tablet or capsule of claim 11, wherein the rice concentrate is present in the tablet or capsule in an amount of about 2% by weight.

18. The tablet or capsule of claim 11, wherein the lecithin is present in the tablet or capsule in an amount of about 33% by weight.

19. The tablet or capsule of claim 11, wherein the rice concentrate acts as a natural silicate and desiccate and an anti-caking agent.

* * * * *